US010231762B2

(12) United States Patent
Steinhauer et al.

(10) Patent No.: US 10,231,762 B2
(45) Date of Patent: Mar. 19, 2019

(54) BONE PLATE SYSTEM

(71) Applicant: Advanced Orthopaedic Solutions, Inc., Torrance, CA (US)

(72) Inventors: Mark A Steinhauer, Redondo Beach, CA (US); J. Tracy Watson, Town and Country, MO (US)

(73) Assignee: Advanced Orthopaedic Solutions, Inc., Torrance, CA (US)

( * ) Notice: Subject to any disclaimer, the term of this patent is extended or adjusted under 35 U.S.C. 154(b) by 192 days.

(21) Appl. No.: 15/057,841

(22) Filed: Mar. 1, 2016

(65) Prior Publication Data

US 2017/0252080 A1 Sep. 7, 2017

(51) Int. Cl.
*A61B 17/80* (2006.01)
*A61B 17/84* (2006.01)

(52) U.S. Cl.
CPC ........ *A61B 17/8004* (2013.01); *A61B 17/809* (2013.01); *A61B 17/8061* (2013.01); *A61B 17/842* (2013.01)

(58) Field of Classification Search
CPC ............................ A61B 17/82; A61B 17/8004
See application file for complete search history.

(56) References Cited

U.S. PATENT DOCUMENTS 3,824,995 A 7/1974 Getscher et al.
5,674,222 A 10/1997 Berger et al.
7,207,993 B1 * 4/2007 Baldwin ................ A61B 17/74 606/300
8,177,822 B2 5/2012 Medoff
8,551,143 B2 10/2013 Norris et al.
8,821,508 B2 9/2014 Medoff et al.
8,961,573 B2 * 2/2015 Gonzalez-Hernandez ................. A61B 17/0401 606/232
9,089,376 B2 7/2015 Medoff et al.
9,220,546 B2 12/2015 Medoff et al.
9,237,911 B2 1/2016 Medoff
9,707,025 B2 * 7/2017 Cavallazzi ............. A61B 17/82
2004/0097942 A1 * 5/2004 Allen ..................... A61B 17/82 606/74

OTHER PUBLICATIONS

TriMed, Ankle Hook Plate, brochure, 2013.
TriMed, Hook Plate Surgical Technique, brochure, 2010.
TriMed, Medial Malleolar Pin Plate, Surgical Technique, brochure, 2013.

* cited by examiner

*Primary Examiner* — Andrew Yang
(74) *Attorney, Agent, or Firm* — Burgess Law Office, PLLC

(57) ABSTRACT

A bone fixation system including a bone plate, a flexible member, and an actuator. The flexible member connected to both the actuator and the bone plate whereby the actuator operates to move or control the movement of the flexible member. In one example, the actuator applies a force to the flexible member placing the flexible member in tension. Correspondingly, the flexible member transmits the force to the bone plate and operates to draw or pull the bone plate toward or to the actuator.

23 Claims, 5 Drawing Sheets

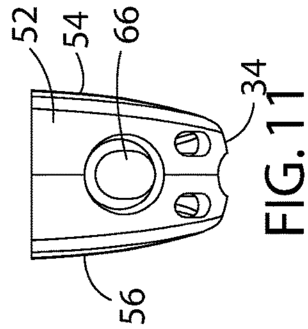
FIG. 11
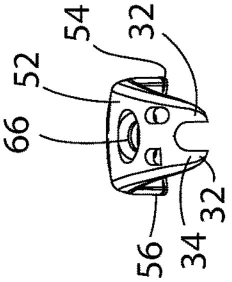
FIG. 8
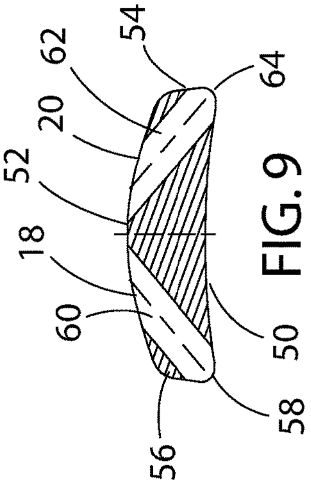
FIG. 9
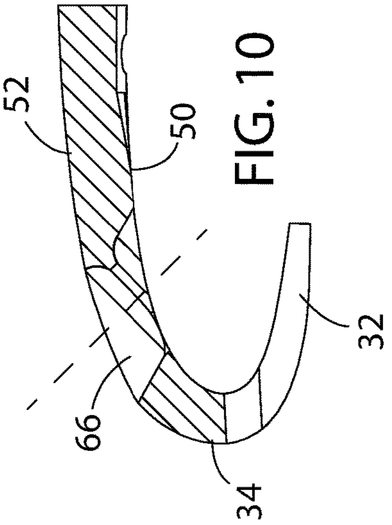
FIG. 10
FIG. 7
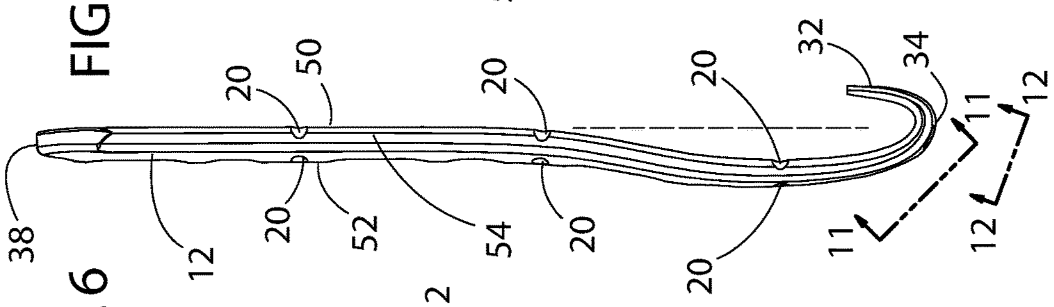
FIG. 6
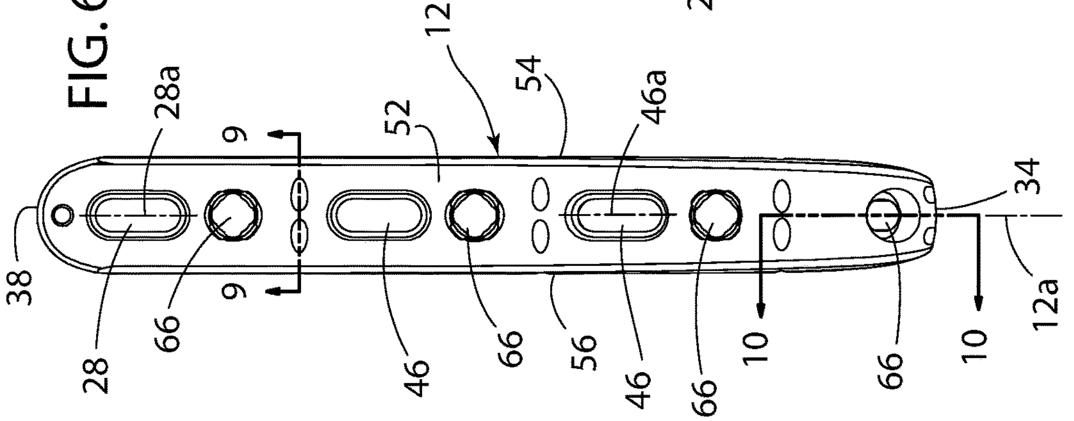

BONE PLATE SYSTEM

CROSS-REFERENCE TO RELATED APPLICATIONS

Not Applicable.

BACKGROUND OF THE INVENTION

1. Field of the Invention

The present disclosure relates generally to bone treatment devices, and more particularly, to a system for compressing and stabilizing a bone fracture.

2. Description of Related Art

Difficulties may arise when repairing bone fractures; in particular fractures adjacent tendons and ligaments, as the tendons and ligaments naturally pull the fragments apart. Such fractures, often coupled with a small bone fragment size, may not provide enough bone or may be a fracture configuration not easily treated with a plate system.

Frequently, a tension band is used for repairing such fractures. Initially, the bone fragments are aligned with guide pins. A wire, typically arranged in a figure eight extends between a screw and the guide pins wherein twisting of the wire compresses the fracture and holds the fragments together.

Bone plates, including those having at least one prong or hook at an end may also be used. Typically, the prong or hook engages the bone fragment. In many cases, the surgeon desires compression between the bone fragments to promote healing. Providing compression when using a bone plate may require use of an additional apparatus or may be limited by current bone plate structure.

SUMMARY OF THE INVENTION

A system for treating a fracture wherein the system includes a bone plate, an actuator, and a flexible member connected to the bone plate and actuator.

A further exemplary embodiment includes a method of reducing a bone fracture by placing a bone plate on the bone, the bone plate spanning the fracture. Locating an actuator on one side of the fracture and attaching the bone plate to the bone on the opposite side of the fracture. Connecting a flexible member to the bone plate and actuator and using the actuator to place the flexible member in tension thereby pulling the plate toward the actuator and reducing the fracture.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 6 is a top view of the bone plate illustrated in FIG. 4.

FIG. 7 is a side view of the bone plate illustrated in FIG. 4.

FIG. 8 is an end view of the bone plate illustrated in FIG. 4.

FIG. 9 is a sectional view taken along line 9-9 of FIG. 6.

FIG. 10 is a sectional view taken along line 10-10 of FIG. 6.

FIG. 11 is a partial end view viewed along line 11-11 of FIG. 7.

DETAILED DESCRIPTION OF THE PREFERRED EMBODIMENTS

The following description of the preferred embodiment(s) is merely exemplary in nature and is in no way intended to limit the invention, its application, or uses.

It must be noted that, as used in this specification and the appended claims, the singular forms "a," "an," and "the" include plural referents unless the context dictates otherwise. In addition, the term "at" when referring to the location or placement of an element or object means in, near or by the area or location occupied by the particular structure or element referred to.

Unless otherwise noted, as used in this specification and the appended claims, the terms "top," "bottom," "side," "end," "left," "right," and/or the like, are used herein solely for reference purposes and are not meant to limit the scope of the present invention.

As used herein, the term "proximal" shall refer broadly to the concept of a nearest portion and the term "distal" shall generally refer to the opposite of proximal, and thus to the concept of a further portion, or a furthest portion, depending upon the context.

Figure 1:
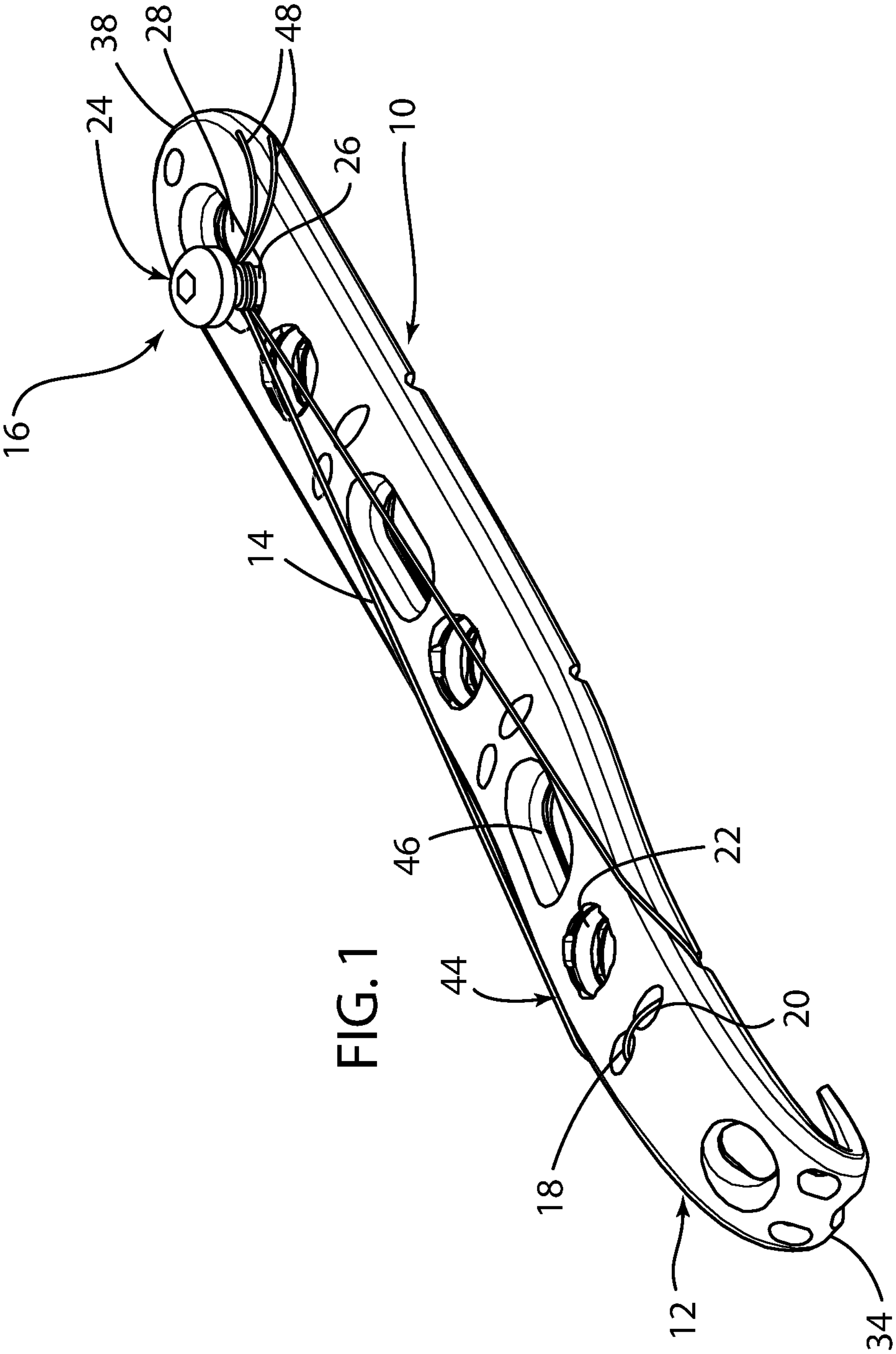
FIG. 1 is a top perspective view of a bone plate system according to the present invention.
Figure 2:
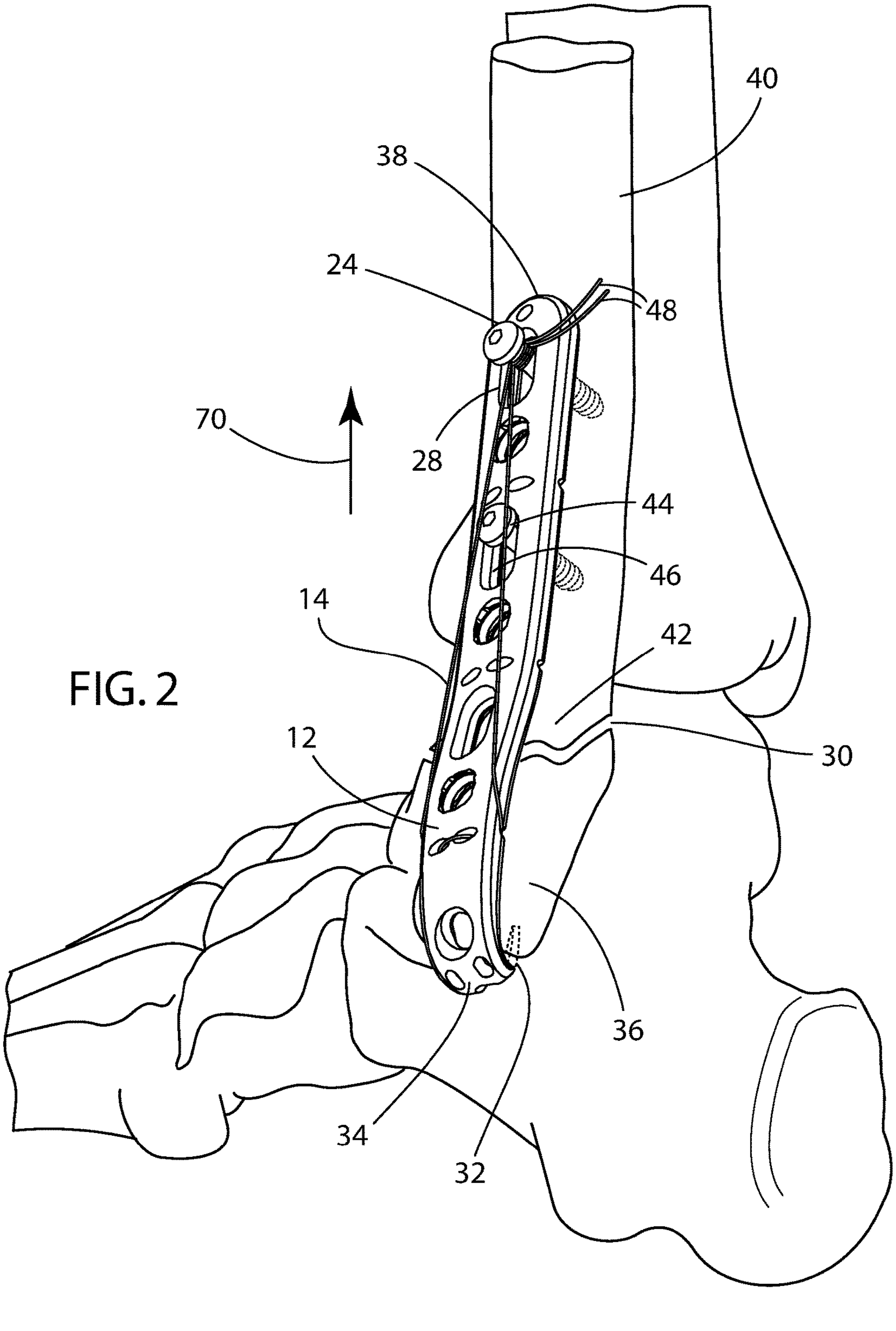
FIG. 2 is a perspective view of the bone plate system according to the present invention placed in an initial assembled condition on [which bone] prior to reducing a fracture.

FIGS. 1-2 illustrate a bone fixation system, seen generally at 10. The bone fixation system 10 is suitable for repairing bone fractures, including for example fractures adjacent tendons and ligaments, as the tendons and ligaments naturally pull the fragments apart. The bone fixation system 10 is suitable for repairing fractures having a small size of bone fragments; as such fractures may not provide enough bone or a fracture configuration enabling treatment with a conventional plate system. It should be understood that the bone plate system 10 may be used to repair different types of fractures and fractures of other bones.

The bone fixation system 10 includes a bone plate 12, a flexible member, seen generally at 14 and an actuator, seen generally at 16.

The bone plate 12 includes a mechanism, illustrated herein as apertures 18, 20 whereby the flexible member 14 connects to the bone plate 12. The flexible member 14 may be, by way of an example, a cable, suture, wire, or other type of tension band. As illustrated, threading the flexible member 14 through the apertures 18, 20 connects the flexible member 14 to the bone plate 12. The flexible member 14 transmits a force applied thereto to the bone plate 12. For example, pulling the flexible member 14 pulls the bone plate 12.

Threading the flexible member 14 through the apertures 18, 20 is one method of connecting the flexible member 14 to the bone plate 12. Other mechanisms or methods may also be used, for example, the flexible member 14 may be threaded through an existing aperture; i.e. slot or other threaded or unthreaded hole in the bone plate 12. In addition, flexible member 14 may be connected to a separate fastener, not shown, that may be inserted into an existing threaded aperture on the bone plate 12. For example, a threaded fastener or bone screw may be partially inserted into the threaded aperture 22 adjacent the apertures 18, 20 with the flexible member 14 connected to or engaging the threaded fastener or bone screw partially inserted into the threaded aperture 22. As illustrated, the bone system 10 includes a mechanism, illustrated in the disclosed example as the apertures 18, 20, for connecting the flexible member 14 to the bone plate 12.

The flexible member 14 further connects to the actuator 16. The actuator 16 operates to move or control the movement of the flexible member 14. Specifically, the actuator 16 applies a force to the flexible member 14 placing the flexible member 14 in tension. Correspondingly, the flexible member 14 applies a tensile force to the bone plate 12 that operates to draw or pull the bone plate 12 toward or to the actuator 16.

One example of an actuator 16 suitable for use with the present invention is a screw 24. As illustrated, the flexible member 14 engages the screw 24. In the disclosed example, a portion of the flexible member 14 wraps around the shank 26 of the screw 24. Wrapping the flexible member 14 around the shank 26 screw 24 engages or releasably connects the flexible member 14 to the screw 24. In the disclosed embodiment, the screw 24 performs as a mechanical actuator whereby rotational motion of the screw 24 is converted into linear motion of the flexible member 14. Linear motion of the flexible member 14 applies a tensile force to the bone plate 12.

In the disclosed example, the screw 24 extends through a slot or elongated aperture 28 in the bone plate 12. Extending the screw 24 through the slot or elongated aperture 28 in the bone plate 12 controls the movement of the bone plate 12. The relative movement between the screw 24 and bone plate 12 is limited to the length of the slot or elongated aperture 28.

While the disclosed embodiment shows the screw 24 placed in a slot or elongated aperture 28 in axial alignment; i.e. along a common longitudinal axis, understanding that the configuration of aperture containing the screw 24 controls the movement of the bone plate, various aperture configurations are also contemplated.

Figure 3:
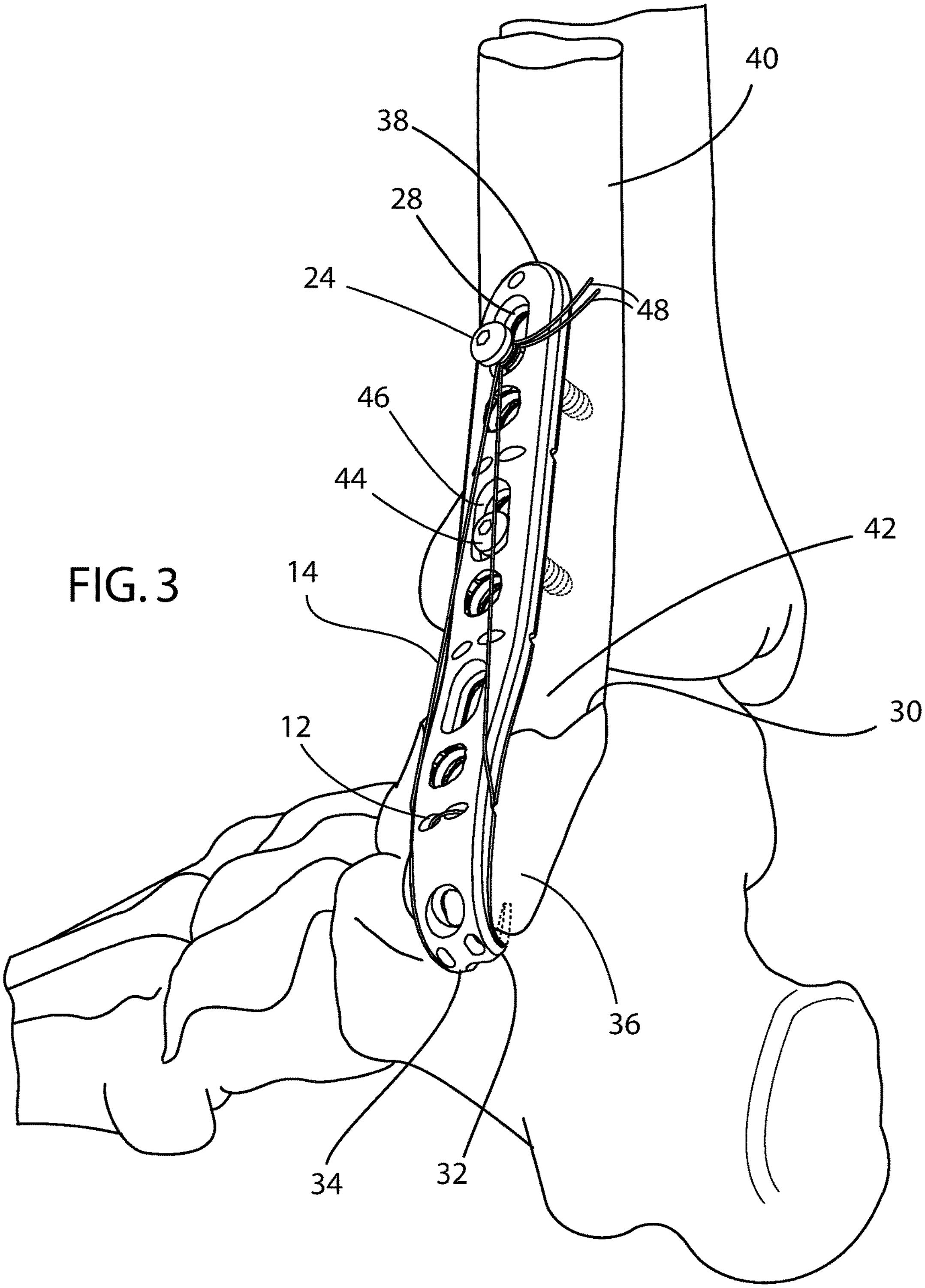
FIG. 3 is a perspective view of the bone plate system according to the present invention shown in an assembled condition on [bone] after reducing a fracture.
Figures 4, 5:
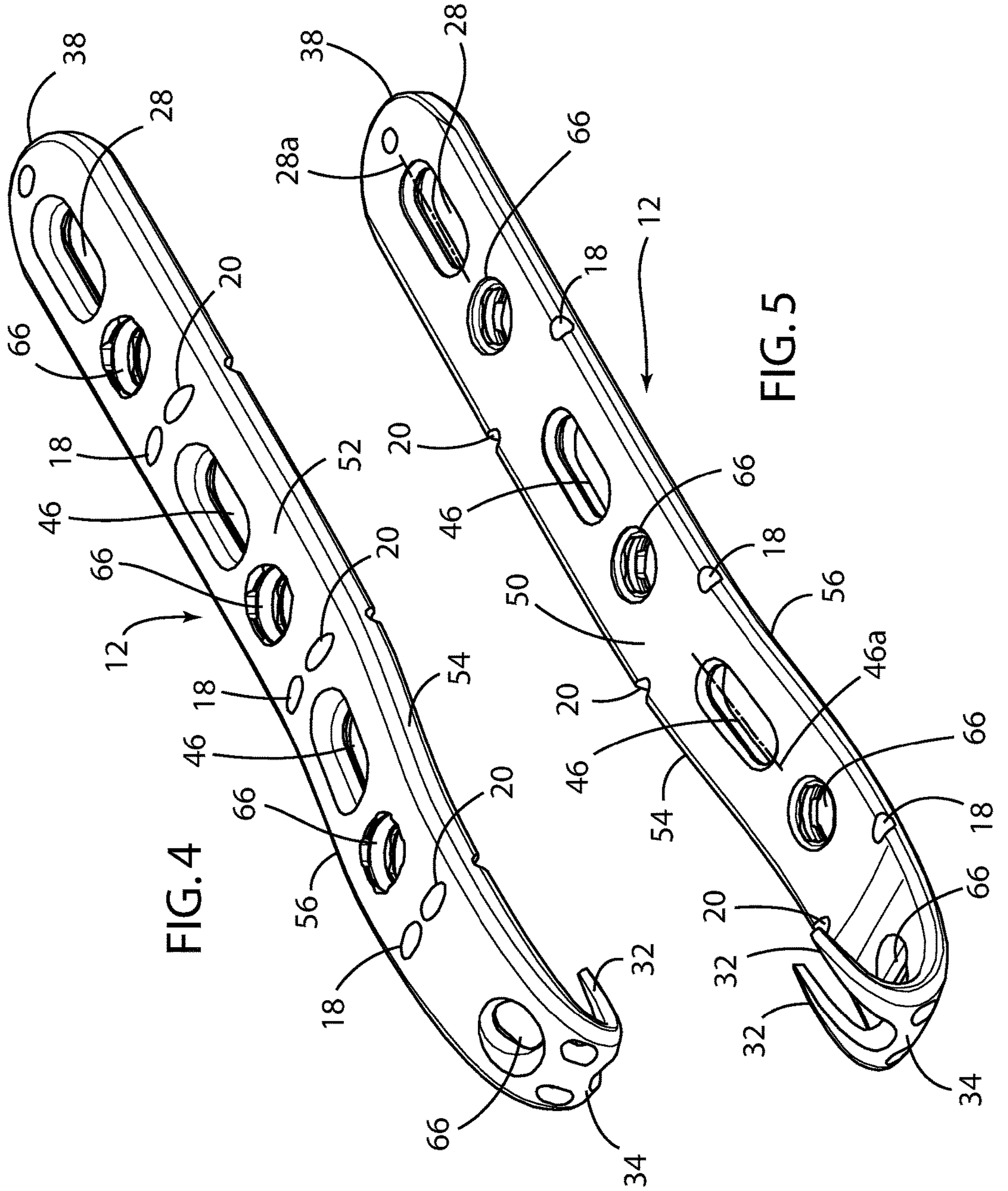
FIG. 4 is a top perspective view of the bone plate illustrated in the bone plate system of FIG. 1.
FIG. 5 is a bottom perspective view of the bone plate of FIG. 4.

FIGS. 2-3 illustrate the bone fixation system 10 of the present invention used to repair a fracture. One example of a bone plate 12 suitable for use with the bone fixation system 10 includes at least one hook member 32 located at a distal end 34 of the bone plate 12. The slot or elongated aperture 28 is located at a proximal end 38 of the bone plate 12. Initially, the bone plate 12 is placed such that it extends across and spans the unreduced fracture 30 wherein the hook member 32 is on one side of the fracture 30 and the slot or elongated aperture 28 is on the opposite or other side of the fracture 30. As illustrated in FIG. 2, the hook member 32 engages the primary bone fragment 36, illustrated in the disclosed example as a fragment of the fibula, securing the bone plate 12 to one side, for example the distal side, of the fracture 30.

After securing the bone plate 12 to, for example, the distal side of the fracture 30 the screw 24 is placed in the slot or elongated aperture 28 of the bone plate 12 on the opposite, proximal side of the fracture 30. The screw 24 is partially threaded into the primary bone 40, illustrated in the disclosed example as the fibula, on the proximal side 42 of the fracture 30 whereby the bone plate 12 is slidably or movably connected to the bone 40 on the proximal side 42. While shown in use with a fibula, bone fixation system 10 of the present invention is suitable for use with different bones and bone fractures.

Next the flexible member 14 is threaded into the apertures 18, 20 in a loop 44 having ends 48 positioned adjacent the screw 24. The ends 48 are wrapped about the shank 26 of the screw 24 in a clockwise manner. The number of wraps or turns of the flexible member 14 about the screw 24 determined as necessary to frictionally engage the flexible member 14 with the screw 24.

Once wrapped about the screw 24, rotation of the screw 24 in a clockwise direction; i.e. tightening the screw 24, causes the flexible member 14 to wind around the shank 26 shortening loop length and drawing the distal end 34 of the bone plate 12 and correspondingly the bone fragment 36 toward the screw 24 as bone plate 12 moves relative to the screw 24.

As illustrated in FIG. **3*a* the bone plate 12 moves upward, wherein the proximal end 38 moves further away from the fracture 30, as illustrated by the change in position of the screw 24 in the slot or elongated aperture 24. The length of the slot or elongated aperture 28 is one factor controlling the amount or degree of reduction applied by the bone plate system 10**.

After the fracture 30 is sufficiently reduced, one or more fixation elements, for example bone screws, extend through openings in the bone plate 12 and are threaded into the bone 40 to secure or fix the bone plate 12 in place. Once the bone plate 12 is sufficiently fixed, the screw 24 may be loosened; i.e. rotated counterclockwise to release tension on the flexible member 14 enabling unwinding of the flexible member 14 from the screw 24. Once unwound from the screw 24, the flexible member 14 may be withdrawn from the bone plate 12 and the screw 24 tightened until it engages the bone plate 12 and aids in securing or fixing the bone plate 12.

In another example, a second screw 44 may be inserted into a second or additional slot or elongated aperture 46. As illustrated, both the first and second slots or elongated apertures 28, 46 each have a longitudinal axis **28*a*, 46*a* extending substantially parallel to the longitudinal axis 12*a* of the bone plate 12. The first and second slots or elongated apertures 28, 46 having a lateral width; i.e. the distance between respective longitudinal sides, slightly greater than the width of the respective shanks of the first and second screws 24, 44.The position of the respective first and second screws 24, 44 on the bone orients the direction of bone plate 12 movement whereby placement of the first and second screws 24, 44** can be used to control direction of fragment travel and corresponding fragment reduction.

In a further example, the bone plate 12 may include additional apertures on the distal end 34 such apertures suitable for receiving locking or nonlocking screws to fix the bone fragment 36.

If desired, instead of loosening the screw 24 and removing the flexible member 14 from the bone plate 12, the screw 24 may be tightened to a position sandwiching the flexible member 14 between the head of the screw 24 and the bone plate 12. Doing so maintains the tension in the flexible member 14. It should be appreciated that the tension applied by the flexible member 14 engaging the screw 24 depends on the frictional coefficient between the flexible member 14 and screw 24. In some situations, it may be advisable to fix the bone plate 12 using screws and the various apertures in the bone plate 12 and then release the tension on the flexible member 14 after which it can be loosely wrapped to the screw 24 and tightened or sandwiched to the bone plate 12. In this manner, if desired, additional tensile force may be applied at a later time without the need to reinsert the flexible member 14.

FIGS. 4-11 illustrate one example of the bone plate 12 suitable for use with the bone plate system 10. The bone plate 12 includes a lower surface 50, an upper surface 52 along with opposing side surfaces 54, 56. The lower surface 50 being the surface closer to, facing toward, and at least partially contacting the bone 40. The upper surface 52 being the surface farther from and facing away from the bone 40. The bone plate 12 including a plurality of additional apertures 66 extending between the lower surface 12 and the upper surface 14. The apertures 66 suitable for receiving fixation elements or fasteners, which may include bone screws and/or the like. Some apertures 66 may receive the bone fixation elements or fasteners at an angle relative to a central or longitudinal axis of the aperture 66. Positioning and securing the fastener in the aperture 66 of the bone plate 12 at various angles enables the surgeon to reach different areas of bone or capture random fragments in various positions.

As illustrated, apertures 18, 20 extend generally at an angle, see FIG. 9, establishing a passageway 60 from a lower corner 58 of the bone plate 12 to the upper surface 52. Orienting the passageway 60 in this manner enables a surgeon to access the respective apertures 18, 20 when the bone plate 12 is secured against the bone. Using a curved needle, a surgeon may thread the flexible member 14, starting at the lower corner 58 through the passageway 60 and out past the upper surface 52. The surgeon then inserts the needle into the aperture 20 in the upper surface 52 through the passageway 62 and out of the passageway 62 at the opposite lower corner 64. The flexible member 14 is then pulled through and the respective ends are wrapped about the screw 24.

As illustrated, the bone plate 12 may include multiple pairs of apertures 18, 20 at various positions on the bone plate 12 to assist in reducing fractures at different locations.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A system for treating a fracture comprising:
- a bone plate having an elongated aperture;
- an actuator disposed in said elongated aperture; and
- a flexible member contacting and extending between said bone plate and said actuator.

2. The system of claim 1 including:
- said bone plate having a longitudinal axis;
- said actuator including a screw extending through said elongated aperture; and
- said flexible member contacting said screw.

3. The system of claim 2 wherein a slot forms said aperture, said slot having a longitudinal axis parallel to the longitudinal axis of said bone plate.

4. The system of claim 1 wherein said bone plate includes a plurality of threaded apertures.

5. The system of claim 1 wherein said bone plate includes at least one hook.

6. The system of claim 1 wherein said bone plate includes a portion laterally offset from said longitudinal axis.

7. The system of claim 6 wherein said portion laterally offset from said longitudinal axis includes a hook.

8. The system of claim 1 wherein said flexible member is a cable, suture, wire, polymer or like member.

9. The system of claim 2 including a second aperture wherein said aperture is a slot and said second aperture is a slot, both slots extending longitudinally in a direction parallel to the longitudinal axis of said plate.

10. The system of claim 2 whereby said flexible member frictionally engages said screw whereby rotation of said screw winds said flexible member around said screw.

11. The system of claim 2 wherein said bone plate includes a second aperture and said flexible member extends through said second aperture.

12. The system of claim 11 wherein said second aperture is accessible after said bone plate is placed on said bone such that said flexible member connects to said bone plate after said bone plate is placed on said bone.

13. A method for reducing a bone fracture comprising the steps of:
- placing a bone plate on said bone and spanning said fracture whereby a proximal end is located on one side of the fracture and a distal end is located on the other side of said fracture;
- attaching the bone plate to the bone on one side of the fracture;
- connecting a flexible member to the bone plate and an actuator and using the actuator to place the flexible member in tension thereby pulling said plate toward the actuator and reducing the fracture.

14. The method of claim 13 including the steps of:
- providing the bone plate with a slot, wherein the slot is located on one side of the fracture;
- inserting a screw through said slot into said bone on one side of the fracture;
- attaching the bone plate to the bone on the opposite side of the fracture;
- connecting the flexible member to the bone plate and the screw and rotating the screw to place the flexible member in tension.

15. The method of claim 14 including the step of using additional screws to anchor the bone plate to the bone; and
- after the bone plate is anchored, releasing the tension on the flexible member, removing the flexible member, and tightening the screw previously placing the flexible member in tension such that it engages the bone plate.

16. The method of claim 13 including the step of providing apertures in said bone plate, said apertures accessible after said bone plate is placed on said bone such that said flexible member connects to said bone plate after said bone plate is placed on said bone.

17. A fracture fixation device comprising:
- a bone plate having a longitudinal axis, a top surface, a bottom surface;
- said bone plate having a slot having a longitudinal axis, said longitudinal axis substantially parallel to said longitudinal axis of said bone plate, said slot forming an opening extending between said top surface and said bottom surface of said bone plate;
- said bone plate having an engagement portion, said engagement portion suitable for receiving a flexible member; and
- an actuator transmitting a force to said bone plate through said flexible member to vary a position of said bone plate relative to said actuator.

18. The fixation device of claim 17 wherein said engagement portion includes an aperture in said bone plate, said aperture sized to receive the flexible member.

19. The fixation device of claim 17 including a plurality of threaded apertures suitable for receiving bone screws.

20. The fixation device of claim 17 including an engagement member, said engagement member suitable for engaging one end of said bone plate to bone.

21. The fixation device of claim 17 including a screw located in said slot.

22. The fixation device of claim 17 wherein said actuator includes a screw, said flexible member connected to said screw such that rotation of said screw causes linear motion of the flexible member.

23. A fracture fixation device comprising:

a bone plate having a longitudinal axis, a top surface, a bottom surface;

said bone plate having a plurality of apertures suitable for receiving bone screws;

a tension member connected to said bone plate; and an actuator connected to said tension member and transmitting a force to said bone plate through said tension member to vary a position of said bone plate relative to said actuator.

* * * * *